(12) United States Patent
Dobschal et al.

(10) Patent No.: US 7,525,115 B2
(45) Date of Patent: Apr. 28, 2009

(54) ARRANGEMENT FOR INSPECTING OBJECTS, ESPECIALLY MASKS IN MICROLITHOGRAPHY

(75) Inventors: Hans-Juergen Dobschal, Kleinromstedt (DE); Wolfgang Harnisch, Lehesten (DE); Thomas Scheruebl, Jena (DE); Nobert Rosenkranz, Reichenbach (DE); Ralph Semmler, Jena (DE)

(73) Assignee: Carl Zeiss SMS GmbH, Jena (DE)

( * ) Notice: Subject to any disclaimer, the term of this patent is extended or adjusted under 35 U.S.C. 154(b) by 64 days.

(21) Appl. No.: 10/554,048

(22) PCT Filed: Apr. 20, 2004

(86) PCT No.: PCT/EP2004/004161

§ 371 (c)(1),
(2), (4) Date: Oct. 24, 2005

(87) PCT Pub. No.: WO2004/095136

PCT Pub. Date: Nov. 4, 2004

(65) Prior Publication Data
US 2006/0262306 A1    Nov. 23, 2006

(30) Foreign Application Priority Data
Apr. 24, 2003   (DE) ................ 103 18 560

(51) Int. Cl.
G01N 23/04     (2006.01)
G01N 21/00     (2006.01)

(52) U.S. Cl. ...................... 250/580; 356/337

(58) Field of Classification Search ................. 250/580, 250/396 R, 591; 356/337
See application file for complete search history.

(56) References Cited

U.S. PATENT DOCUMENTS 3,917,950 A    11/1975   Carlson (Continued)

FOREIGN PATENT DOCUMENTS

DE    19929185 A1    6/1999

(Continued)

OTHER PUBLICATIONS

Imada S et al; "Epitaxial Growth of Ferroelectric YMnO$_3$ thin films on Si (111) Substrates by Molecular Beam Epitaxy"; Japanese Journal of Applied Physics; Publication Office Japanese Journal of Applied Physics; Dec. 1998; pp. 6497-6501; vol. 37 No. 12A Part 1; Tokyo.

Primary Examiner—David P Porta
Assistant Examiner—Faye Boosalis
(74) Attorney, Agent, or Firm—Jacobson Holman PLLC

(57) ABSTRACT

Apparatus for inspecting objects especially masks in microlithography that are disposed in a vacuum chamber. The apparatus includes a converter for converting illuminating radiation emitted from the object into a radiation of a higher wavelength. A sensor for recording images is disposed outside the vacuum chamber and arranged as an optical interface from the vacuum chamber to the sensor of the converter or at least one part of an image lens is arranged as a window in the vacuum chamber.

6 Claims, 2 Drawing Sheets

U.S. PATENT DOCUMENTS

| | | | |
|---|---|---|---|
| 5,498,923 A * | 3/1996 | La Fontaine et al. | 313/467 |
| 6,016,185 A * | 1/2000 | Cullman et al. | 355/52 |
| 6,198,095 B1 * | 3/2001 | Staib | 250/287 |
| 6,492,644 B1 | 12/2002 | Staib | |
| 6,555,828 B1 * | 4/2003 | Bokor et al. | 250/492.2 |
| 7,312,459 B2 * | 12/2007 | Amemiya et al. | 250/372 |
| 2001/0012099 A1 | 8/2001 | Kumagai | |
| 2003/0011896 A1 | 1/2003 | Shiraishi | |
| 2004/0070846 A1 * | 4/2004 | Dobschal et al. | 359/795 |
| 2004/0174607 A1 | 9/2004 | Brunner et al. | |
| 2005/0030537 A1 * | 2/2005 | Hayashi et al. | 356/401 |
| 2006/0262306 A1 * | 11/2006 | Dobschal et al. | 356/337 |

FOREIGN PATENT DOCUMENTS

| | | |
|---|---|---|
| DE | 10063239 A1 | 12/2000 |
| DE | 10130212 A1 | 1/2003 |
| EP | 1 063 676 A | 12/2000 |

* cited by examiner

Fig. 1: Embodiment of the complete system
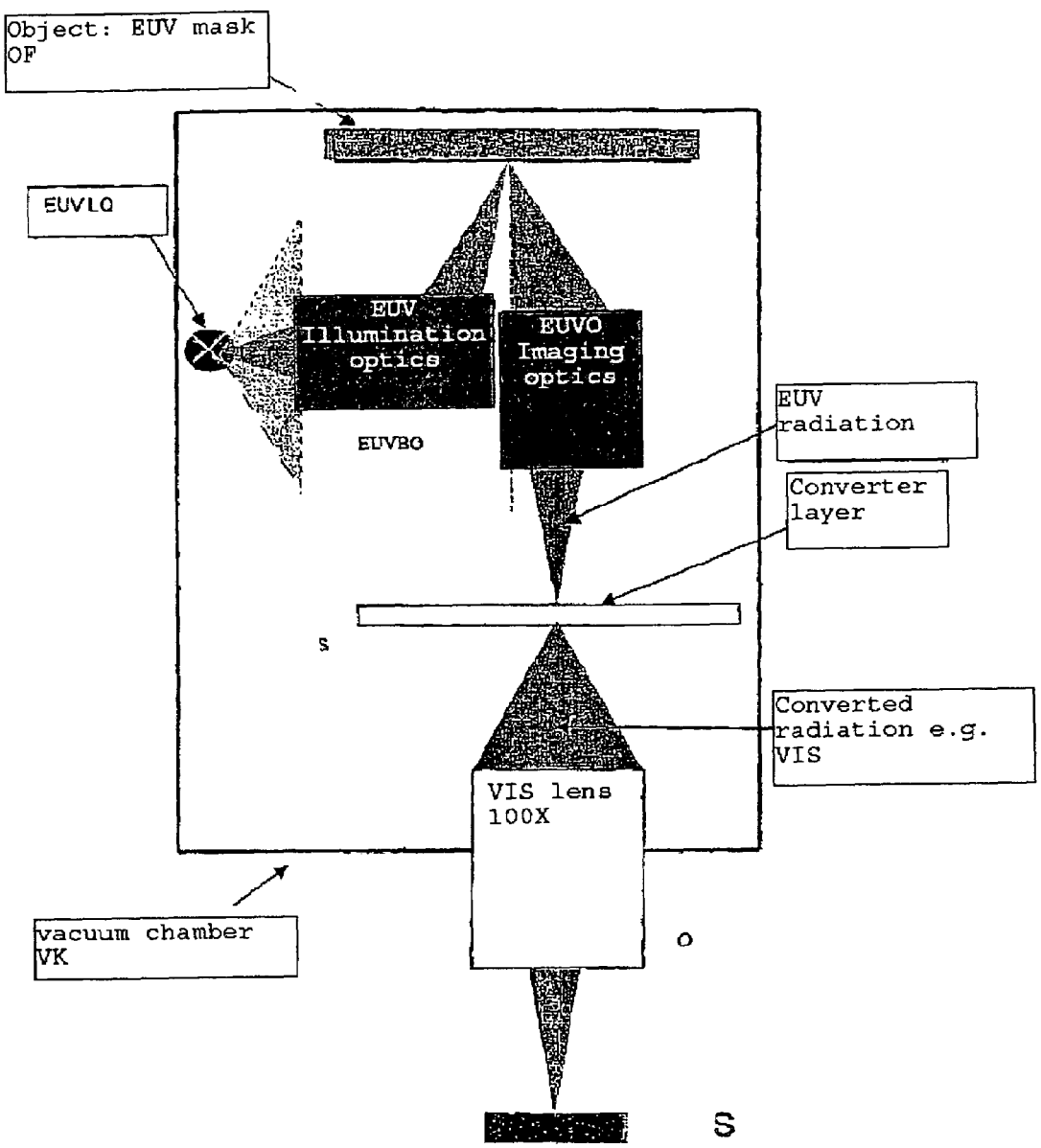

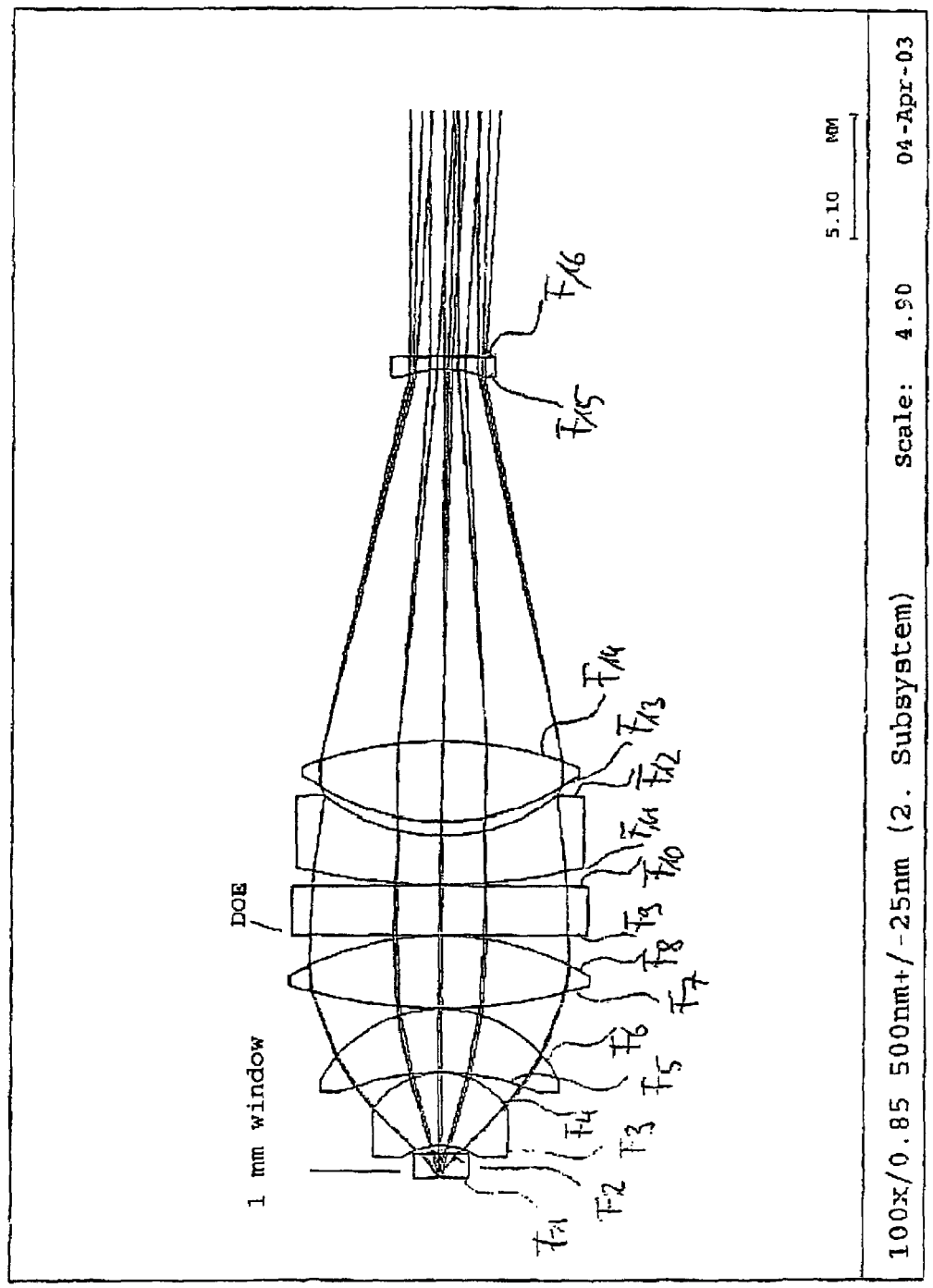

ARRANGEMENT FOR INSPECTING OBJECTS, ESPECIALLY MASKS IN MICROLITHOGRAPHY

CROSS REFERENCE TO RELATED APPLICATIONS

The present patent application is a nationalization of International Application No. PCT/EP2004/004161, filed Apr. 20, 2004, which is based on, and claims priority from, German Application No. DE 103 18 560.7, filed Apr. 24, 2003, both of which are incorporated herein by reference in their entireties.

FIELD OF THE INVENTION

This invention relates to the field of Microlithography and to devices for inspecting objects that are disposed in a vacuum chamber.

BACKGROUND OF THE INVENTION

In order to observe objects or images of objects disposed in vacuum chambers, it is necessary to either insert the observation lens and the sensor (camera) into the vacuum chamber or to observe the objects or images through a vacuum window.

This is particularly required in the case of images using extreme ultraviolet radiation (EUV) if this radiation is converted using scintillators into radiation of a different wavelength and then reproduced on the sensor using additional optics such as described in U.S. Pat. No. 5,498,923.

If the sensor is disposed in the interior of the vacuum chamber, this leads to gas emission of, for example, siloxanes or hydrocarbons from the sensor. This poses a high hazard of contamination of the devices disposed in the vacuum chamber. Optical elements that are exposed to radiation that is rich in energy, particularly EUV radiation, are especially at risk.

If the sensor is disposed outside this vacuum chamber, the radiation used for the image must be guided through a vacuum window onto the sensor. As a result of the window in this case, limitations arise with respect to the quality of the optical images and the usable aperture of the imaging optics.

SUMMARY OF THE INVENTION

This problem of the prior art is solved according to the present invention, in that the scintillator itself forms the window or configures the imaging optics disposed in front of the sensor in such a manner that the imaging optics or a part of them are used to form the vacuum window.

Different configurations are possible depending on the respective tasks:
  a) The imaging lens is vacuum-tight and forms the actual window.
  b) The scintillator forms the vacuum window. The vacuum window can be designed advantageously such that it can be replaced, if the scintillator starts to age.
  c) A part of the lens forms the vacuum window. Here, it is particularly advantageous to configure the first lens of the imaging optics from the source of radiation as the vacuum window because then the remaining parts of the lens are not exposed to the vacuum. Furthermore, the first lens can be permanently arranged in the vacuum chamber and the remainder of the lens can be interchangeable in order to change the imaging conditions, for example for recording an overview image by adding other lens groups.

Using all the specified options, it is possible to arrange the actual sensor that represents a high risk of emissions and contamination outside the vacuum chamber and yet achieve a superior optical imaging quality.

BRIEF DESCRIPTION OF THE DRAWINGS

FIG. 1 is a schematic drawing of an inspection apparatus embodying the subject invention.

FIG. 2 is a schematic diagram of a lens system forming part of the subject invention of FIG. 1.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The present invention is explained more fully on the basis of FIG. 1.

The object field OF illuminated using an EUV source of light LQ via illuminating optics EUVBO is reproduced on a scintillator S by means of EUV optics EUVO. The scintillator converts the image of the EUV wavelength range into an image of a long-wave range, which is then reproduced on the sensor using an image lens O (i.e. micro lens). In doing so, the imaging lens/the scintillator is used according to the invention in one of the configurations described above.

The lens O is illustrated schematically. A first optical element can form the window, which is then followed by other lens elements that are arranged outside the vacuum chamber VK and are not illustrated here.

FIG. 2 illustrates an optical example for the lens O. The lens illustrated is advantageously a cement-free hybrid lens as has been described in detail in DE 10130212 A1. Its advantage is the low material expenditure involved and better optical quality. The use of a diffractive element DOE increases refraction and has an achromatising effect.

The first optical element F1/F2 and also e.g. the DOE F9/F10 can be the window of the vacuum chamber here.

Data regarding the hybrid lens (mm)

| Surface | Radius | Thickness | Material |
| --- | --- | --- | --- |
| F1 | unlimited | | |
| | | 1.000 | Q1 (synthetic quartz) |
| F2 | Unlimited | | |
| | | 0.3028 | Air |
| F3 | −2.744 | | |
| | | 2.9773 | Bk10 |
| F4 | −3.116 | | |
| | | 0.0200 | Air |
| F5 | −9.911 | | |
| | | 2.5723 | Bk7 |
| F6 | −5.292 | | |
| | | 0.0500 | Air |
| F7 | 19.699 | | |
| | | 2.9207 | Bk7 |
| F8 | −11.828 | | |
| | | 0.0500 | Air |
| F9 | Unlimited | | |
| | | 2.0033 | Bk7 |
| F10 | Unlimited | | |
| F11 | 23.072 | | |
| | | 2.000 | Nsf6 |

-continued

| Surface | Radius | Thickness | Material |
|---------|--------|-----------|----------|
| F12 | 7.541 | | |
| | | 0.5624 | Air |
| F13 | 9.051 | | |
| | | 3.2297 | Psk53a |
| F14 | −15.148 | | |
| | | 15.2701 | Air |
| F15 | −4.369 | | |
| | | 0.500 | Ssk2 |
| F16 | −117.556 | | |

. . . etc. to the tube lens (not illustrated)

It is to be understood that the present invention is not limited to the illustrated embodiments described herein. Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

The invention claimed is:

1. Apparatus for inspecting a mask used in microlithography, the apparatus comprising:
    a vacuum chamber;
    illuminating means for illuminating a mask in the vacuum chamber with extreme ultraviolet light, the illuminating means being disposed inside the vacuum chamber;
    converter means for converting an image in extreme ultraviolet radiation emitted by the mask into an image in radiation of a longer wavelength, the converter means being disposed inside the vacuum chamber;
    sensor means for recording the image in the radiation of a longer wavelength, the sensor means being disposed outside the vacuum chamber; and
    an optical interface from the vacuum chamber to the sensor means, the optical interface being arranged as a vacuum window in the vacuum chamber.

2. The apparatus of claim 1, wherein the converter means comprises a scintillator.

3. The apparatus of claim 1, wherein the converter means forms the optical interface from the vacuum chamber to the sensor means and is arranged as a window in the vacuum chamber.

4. The apparatus of claim 1, further comprising imaging optic means disposed in front of the sensor means for reproducing the longer wavelength image on the sensor means, wherein:
    at least a part of the imaging optic means is disposed inside the vacuum chamber, and
    at least a part of the imaging optic means forms the optical interface from the vacuum chamber to the sensor means and is arranged as a window in the vacuum chamber.

5. The apparatus of claim 4, wherein the imaging optic means is vacuum-tight and forms the optical interface.

6. The apparatus of claim 5, where the imaging optic means includes a cement-free hybrid lens having at least one diffractive optical element.

* * * * *